US012089955B2

(12) United States Patent
Conn

(10) Patent No.: US 12,089,955 B2
(45) Date of Patent: Sep. 17, 2024

(54) SYSTEMS, DEVICES, AND METHODS FOR MONITORING LOADS AND FORCES ON A SEAT

(71) Applicant: Casana Care, Inc., Rochester, NY (US)

(72) Inventor: Nicholas Joseph Conn, Fairport, NY (US)

(73) Assignee: Casana Care, Inc., Rochester, NY (US)

( * ) Notice: Subject to any disclaimer, the term of this patent is extended or adjusted under 35 U.S.C. 154(b) by 0 days.

(21) Appl. No.: 17/885,299

(22) Filed: Aug. 10, 2022

(65) Prior Publication Data
US 2022/0378373 A1 Dec. 1, 2022

Related U.S. Application Data

(63) Continuation of application No. PCT/US2022/024236, filed on Apr. 11, 2022.

(60) Provisional application No. 63/172,903, filed on Apr. 9, 2021.

(51) Int. Cl.
A61B 5/00 (2006.01)
A61B 5/0205 (2006.01)
A61B 5/0245 (2006.01)
A61B 5/11 (2006.01)
G01G 19/44 (2006.01)

(52) U.S. Cl.
CPC .......... *A61B 5/6891* (2013.01); *A61B 5/0205* (2013.01); *A61B 5/0245* (2013.01); *A61B 5/1102* (2013.01); *A61B 5/7203* (2013.01); *G01G 19/44* (2013.01)

(58) Field of Classification Search
CPC ... A61B 5/6891; A61B 5/0205; A61B 5/1102; G01G 19/44
See application file for complete search history.

(56) References Cited

U.S. PATENT DOCUMENTS

| 4,203,497 | A | 5/1980 | Harris et al. |
| 4,212,361 | A | 7/1980 | Stocker |
| 4,697,656 | A | 10/1987 | De Canecaude |
| 4,711,313 | A | 12/1987 | Lida et al. |
| 4,969,112 | A | 11/1990 | Castle |

(Continued)

FOREIGN PATENT DOCUMENTS

| CA | 1324415 C | 11/1993 |
| CN | 100502773 C | 6/2009 |

(Continued)

OTHER PUBLICATIONS

International Search Report and Written Opinion for Application No. PCTUS2022029646, mailed on Nov. 3, 2022, 23 pages.

(Continued)

*Primary Examiner* — John R Downey
(74) *Attorney, Agent, or Firm* — Cooley LLP

(57) ABSTRACT

Systems, devices, and methods are disclosed herein for monitoring physiological data of subjects seated on a toilet, including systems, devices, and methods for monitoring loads and forces on a toilet seat. In some embodiments, systems, devices, and methods disclosed herein include a set of sensors that can measure loads and forces present at coupling points between a toilet seat and a base or other components of a toilet.

17 Claims, 9 Drawing Sheets

(56) References Cited

U.S. PATENT DOCUMENTS

| | | | |
|---|---|---|---|
| 6,727,438 B1 | 4/2004 | Stokes | |
| 7,437,781 B2 | 10/2008 | Rigas | |
| 7,521,638 B1 | 4/2009 | Godshaw et al. | |
| 8,827,918 B2 | 9/2014 | Kim et al. | |
| 8,983,854 B2 | 3/2015 | Park et al. | |
| 9,595,185 B1* | 3/2017 | Hall | G01G 19/50 |
| 9,829,311 B1 | 11/2017 | Wilson et al. | |
| 9,927,302 B1* | 3/2018 | Hall | A47K 13/24 |
| 10,292,658 B2 | 5/2019 | Borkholder et al. | |
| 11,234,651 B2 | 2/2022 | Borkholder et al. | |
| 11,650,094 B2 | 5/2023 | Borkholder et al. | |
| 2002/0188205 A1 | 12/2002 | Mills | |
| 2003/0233034 A1 | 12/2003 | Varri et al. | |
| 2004/0112149 A1 | 6/2004 | Gebert | |
| 2005/0228305 A1 | 10/2005 | Nagata et al. | |
| 2006/0111641 A1 | 5/2006 | Manera et al. | |
| 2006/0258915 A1 | 11/2006 | Ueda et al. | |
| 2008/0194975 A1 | 8/2008 | MacQuarrie et al. | |
| 2010/0094147 A1 | 4/2010 | Inan et al. | |
| 2013/0310700 A1 | 11/2013 | Wiard et al. | |
| 2014/0039330 A1 | 2/2014 | Seo et al. | |
| 2014/0142396 A1 | 5/2014 | Ricks et al. | |
| 2014/0142437 A1 | 5/2014 | Inan et al. | |
| 2014/0142451 A1 | 5/2014 | Kim et al. | |
| 2016/0317043 A1 | 11/2016 | Campo et al. | |
| 2016/0331244 A1 | 11/2016 | Barton-Sweeney | |
| 2016/0374618 A1 | 12/2016 | Giovangrandi | |
| 2016/0374619 A1 | 12/2016 | Borkholder et al. | |
| 2017/0172421 A1* | 6/2017 | Dabby | G06F 3/011 |
| 2018/0020984 A1 | 1/2018 | Hall et al. | |
| 2018/0042386 A1 | 2/2018 | Hall et al. | |
| 2018/0084960 A1* | 3/2018 | Iwabata | A47K 13/24 |
| 2018/0153414 A1 | 6/2018 | Hall et al. | |
| 2019/0008457 A1 | 1/2019 | Hall et al. | |
| 2019/0008567 A1 | 1/2019 | Barry | |
| 2019/0178704 A1 | 6/2019 | Lui | |
| 2019/0231271 A1* | 8/2019 | Borkholder | A47K 13/24 |
| 2019/0298316 A1 | 10/2019 | Kashyap et al. | |
| 2020/0289000 A1 | 9/2020 | Hall et al. | |
| 2020/0390367 A1 | 12/2020 | Hall et al. | |
| 2020/0390422 A1 | 12/2020 | Hall et al. | |
| 2022/0218286 A1 | 7/2022 | Borkholder et al. | |
| 2022/0346720 A1 | 11/2022 | David et al. | |
| 2022/0361754 A1 | 11/2022 | Borkholder et al. | |
| 2022/0364904 A1 | 11/2022 | Borkholder et al. | |
| 2023/0240485 A1 | 8/2023 | Kashyap et al. | |

FOREIGN PATENT DOCUMENTS

| | | |
|---|---|---|
| CN | 203042108 U | 7/2013 |
| CN | 102660988 B | 3/2014 |
| CN | 210123304 U | 3/2020 |
| DE | 102010061035 A1 | 6/2012 |
| EP | 1488739 A1 | 12/2004 |
| JP | H04367638 A | 12/1992 |
| JP | 2000254040 A | 9/2000 |
| JP | 2010172498 A | 8/2010 |
| JP | 2020153896 A | 9/2020 |
| KR | 20170125696 A | 11/2017 |
| WO | WO-2005070288 A1 | 8/2005 |
| WO | WO-2020172645 A1 | 8/2020 |
| WO | WO-2021055681 A1 | 3/2021 |
| WO | WO-2022217140 A1 | 10/2022 |
| WO | WO-2022240999 A1 | 11/2022 |
| WO | WO-2022245834 A1 | 11/2022 |

OTHER PUBLICATIONS

Non-Final Office Action for U.S. Appl. No. 17/851,938 mailed on Mar. 10, 2023, 21 pages.

Advisory Action mailed Nov. 13, 2018 for U.S. Appl. No. 15/190,534, 4 pages.

Arias, D. E. et al., "Data collection capabilities of a new non-invasive monitoring system for patients with advanced multiple sclerosis," AMIA Annual Symposium Proceedings, 2013:61-68 (2013).

Baek, H. J. et al., System for Unconstrained ECG Measurement on a Toilet Seat using Capacitive Coupled Electrodes: The Efficacy and Practicality, Annu Int Conf IEEE Eng Med Biol Soc., Aug. 20-24, 2008; pp. 2326-2328, Vancouver, British Columbia, Canada.

Chen, Z. et al., "Noninvasive Monitoring of Blood Pressure Using Optical Ballistocardiography and Photoplethysmograph Approaches," 35th Annual International Conference of the IEEE EMBS, Jul. 3-7, 2013, pp. 2425-2428, Osaka, Japan.

Final Office Action mailed Oct. 6, 2017 for U.S. Appl. No. 15/190,534, 6 pages.

Final Office Action mailed Sep. 4, 2018 for U.S. Appl. No. 15/190,534, 9 pages.

Huang, J.-J. et al., "Development of the smart toilet equipment with measurements of physiological parameters," 2012 9th International Conference on Ubiquitous Intelligence and Computer and 9th International Conference on Autonomic and Trusted Computing, 2012, pp. 9-16; doi:10.1109/UIC-ATC.2012.143.

Inan, O. T. et al., "Robust ballistocardiogram acquisition for home monitoring," Physiol Meas, 30(2):169-85 (2009); doi:10.1088/0967-3334/30/2/005.

International Search Report and Written Opinion for Application No. PCT/US2022/024236, mailed on Sep. 12, 2022, 24 pages.

International Search Report and Written Opinion for International Application No. PCT/US2022/028787, mailed Aug. 5, 2022, 23 Pages.

Invitation to Pay Additional Fees for International Application No. PCT/US2022/024236, mailed Jul. 20, 2022, 19 pages.

Invitation to Pay Additional Fees mailed Sep. 9, 2022 for International Application No. PCT/US2022/029646, 15 pages.

Javaid, A. Q. et al., "Quantifying and Reducing Posture-Dependent Distortion in Ballistocardiogram Measurements," IEEE Journal of Biomedical and Health Informatics, 19(5):1549-1556 (2015).

Junilla, S. et al., "An EMFi-film sensor based ballistocardiographic chair: performance and cycle extraction method," IEEE Workshop on Signal Processing Systems Design and Implementation, 2005, pp. 373-377.

Kim, J. S. et al., "A new approach for non-intrusive monitoring of blood pressure on a toilet seat," Physiological Measurement, 27:203-211 (2006).

Kim, J. S. et al., "Multi-channel measurement of photo-plethysmography and evaluation for the optimal site of a thigh in a toilet," 26th Annual International Conference of the IEEE, Sep. 1-5, 2004, pp. 3366-3368, San Francisco, California, USA.

Kim, K. K. et al., "The electrically noncontacting ECG measurement on the toilet seat using the capacitively-coupled insulated electrodes," The 26th Annual International Conference of the IEEE Engineering in Medicine and Biology Society, San Francisco, CA, USA, 2004, pp. 2375-2378, doi:10.1109/IEMBS.2004.1403688.

Lim, Y.G. et al., "Capacitive Measurement of ECG for Ubiquitous Healthcare," Annals of Biomedical Engineering, 42(11):2218-2227 (2014).

Motoi, K. et al., "Development and Clinical Evaluation of a Home Healthcare System Measuring in Toilet, Bathtub and Bed without Attachment of Any Biological Sensors," Proceedings of the 10th IEEE International Conference on Information Technology and Applications in Biomedicine, Corfu, Greece, 2010, pp. 1-4, doi:10.1109/ITAB.2010.5687774.

Motoi, K. et al, "Development of a fully automated network system for long-term health-care monitoring at home," Proceedings of the 29th Annual International Conference of the IEEE EMBS, Aug. 23-26, 2007, pp. 1826-1829, Cite Internationale, Lyon, France.

Non-Final Office Action mailed Dec. 1, 2020 for U.S. Appl. No. 16/377,938, 9 pages.

Non-Final Office Action mailed Feb. 22, 2018 for U.S. Appl. No. 15/190,534, 9 pages.

Non-Final Office Action mailed Jan. 26, 2017 for U.S. Appl. No. 15/190,534, 6 pages.

Non-Final Office Action mailed Jul. 6, 2020 for U.S. Appl. No. 16/377,938, 10 pages.

(56) References Cited

OTHER PUBLICATIONS

Non-Final Office Action mailed Sep. 15, 2022 for U.S. Appl. No. 17/845,883, 11 pages.
Park, K. S., "Nonintrusive Measurement of Biological Signals for Ubiquitous Healthcare," 31st Annual International Conference of the IEEE EMBS, Sep. 2-6, 2009, pp. 6573-6575, Minneapolis, Minnesota, USA.
Prisk, G. K. et al., "Three-dimensional ballistocardiography and respiratory motion in sustained microgravity," Aviation Space and Environmental Medicine, 72(12):1067-1074 (2002).
Schlebusch, T., "Unobtrusive Health Screening on an Intelligent Toilet Seat," ACTA Polytechnica, 51(5):94-99 (2011); http://www.tk.de/tk/innovative-verfahren/telemedizin/herz/9784.
Shin, J. H. et al., "Ubiquitous House and Unconstrained Monitoring Devices for Home Healthcare System," 2007 6th International Special Topic Conference on Information Technology Applications in Biomedicine, Tokyo, Japan, 2007, pp. 201-204, doi:10.1109/ITAB.2007.4407381.
Tanaka, S. et al., "Fully Automatic System for Monitoring Blood Pressure from a Toilet Seat Using Volume-Oscillometric Method," Proceedings of the 2005 IEEE Engineering in Medicine and Biology, 27th Annual Conference, Sep. 1-4, 2005, pp. 3939-3941, Shanghai, China.
Tavakolian, K. et al., "Comparative analysis of infrasonic cardiac signals," Computers in Cardiology, 36:757-760 (2009).
Togawa, T. et al., "Physiological Monitoring Systems Attached to the Bed and Sanitary Equipment," Images of the Twenty-First Century. Proceedings of the Annual International Engineering in Medicine and Biology Society, Seattle, WA, USA, 1989, pp. 1461-1463 vol. 5, doi: 10.1109/IEMBS.1989.96289.
Weber, T. et al., "Noninvasive determination of carotid-femoral pulse wave velocity depends critically on assessment of travel distance: a comparison with invasive measurement," Journal of Hypertension, 27(8):1624-1630 (2009).
Yamakoshi, K. et al., "Non-conscious and Automatic Acquisition of body and Excreta Weight Together with Ballistocardiogram in a Lavatory," 18th Annual International Conference of the IEEE Engineering in Medicine and Biology Society, 1996, pp. 67-68, Amsterdam, 1.1.6:Home Health Monitoring.
Final Office Action for U.S. Appl. No. 17/851,938 dated Jun. 28, 2023, 22 pages.
Non-Final Office Action for U.S. Appl. No. 17/557,264 dated Aug. 16, 2023, 21 pages.
Non-Final Office Action for U.S. Appl. No. 18/130,286 dated Feb. 15, 2024, 9 pages.

\* cited by examiner

SYSTEMS, DEVICES, AND METHODS FOR MONITORING LOADS AND FORCES ON A SEAT

CROSS-REFERENCE TO RELATED APPLICATIONS

This application is a continuation of International Patent Application No. PCT/US2022/024236, entitled "Systems, Devices, and Methods for Monitoring Loads and Forces on a Seat." filed Apr. 11, 2022, which claims the benefit of U.S. Provisional Patent Application Ser. No. 63/172,903, entitled "Systems, Devices, and Methods for Monitoring Loads and Forces on a Seat," filed Apr. 9, 2021, the disclosures of which is are incorporated by reference herein in their entireties.

TECHNICAL FIELD

The embodiments described herein relate generally to health monitoring systems, and more particularly to systems and methods for monitoring physiological characteristics of subjects seated on a toilet or other waste receptacle, including systems and methods for monitoring loads and forces on a toilet seat.

BACKGROUND

Patient health monitoring is an important tool in tracking physiological conditions of patients and to provide early warnings or guidance to individuals and healthcare providers in cases of patient health deterioration. Oftentimes, patient monitoring is obtrusive and requires individuals to actively wear certain devices or change their routine to be able to measure certain vital signs or characteristics of the patient. Unobtrusive systems for monitoring individuals are also limited and can provide inaccurate results. Therefore, there exists a need to develop more accurate approaches to monitoring individuals through unobtrusive means.

SUMMARY

Systems, devices, and methods are described herein for monitoring data (e.g., loads or forces) of individuals seated on a toilet.

In some embodiments, an apparatus includes: a base defining a space for receiving waste; a ring disposed on a surface of the base, the ring including a set of supports configured to engage the surface of the base, the ring including a surface on which a subject can be seated; a coupler configured to couple the ring to the base; a set of sensors including at least one sensor disposed in each support from the set of supports and a sensor disposed along the coupling between the ring and the base, the set of sensors collectively configured to measure forces present on the ring when the subject is seated on the surface of the ring; and a processor, configured to determine at least one of a weight, ballistocardiogram (BCG), or posture of the subject based on the signals.

In some embodiments, a kit includes a ring including a platform and a set of supports, the ring configured to be attached to a coupler that can couple the ring to a base of a toilet such that the set of supports are configured to engage a surface of the base, the platform being disposed at the attachment between the ring and the coupler, where the ring including a set of sensors, the set of sensors including a sensor disposed at each support from the set of supports and a sensor disposed adjacent to the platform, the set of sensors collectively configured to measure total forces present on the ring when the ring is coupled to the base and a subject is seated on a surface of the ring.

In some embodiments, a kit includes: a ring including a set of supports, the ring configured to be coupled to a base of a toilet such that the set of supports are configured to engage a surface of the base, the ring including a first set of sensors including a sensor disposed at each support from the set of supports; and a coupler configured to couple the ring to the base, the coupler including a platform and a second set of sensors disposed adjacent to the platform, the first and second sets of sensors configured to measure total forces present on the ring when the ring is coupled to the base and a subject is seated on a surface of the ring.

In some embodiments, a kit includes a seat attachment configured to couple to a ring or a base of a toilet, the seat attachment including: a surface on which a subject can be seated when the seat attachment is coupled to the ring or the base; and a set of sensors disposed at each point of engagement between the seat attachment and the ring or the base, the set of sensors configured to measure total forces present on the seat attachment when the seat attachment is coupled to the ring or the base and a subject is seated on the surface of the seat attachment.

DETAILED DESCRIPTION

Figure 1A:
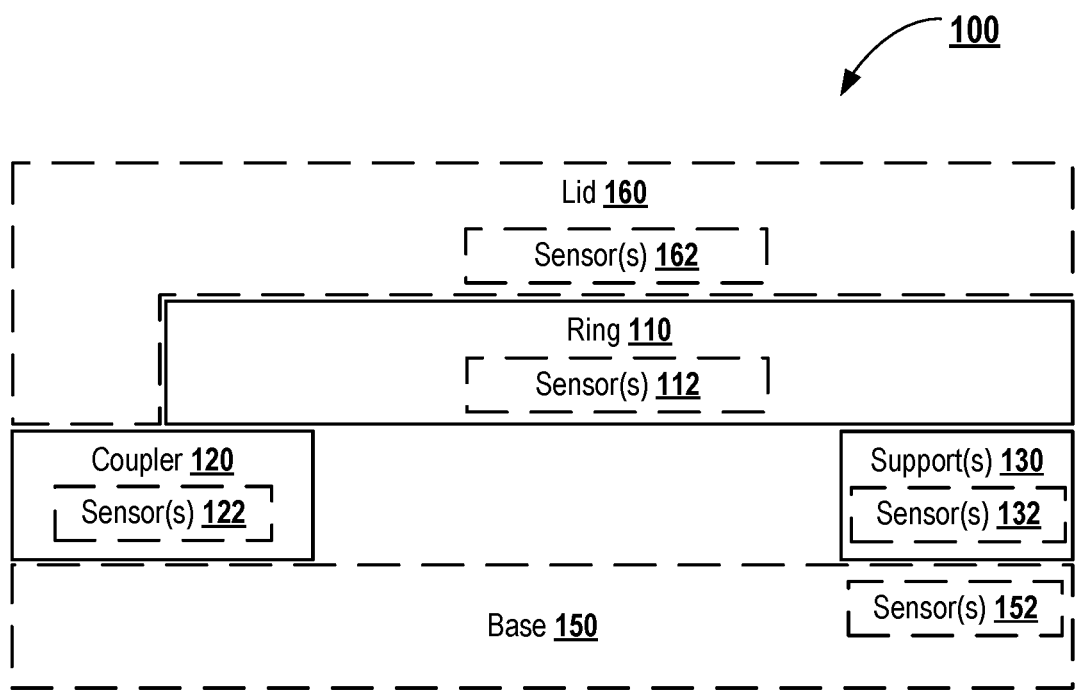
FIG. 1A is a schematic illustration of a device for monitoring signals (e.g., loads or forces) present on a toilet, according to an embodiment.

The embodiments described herein relate generally to health monitoring systems and devices, and more particularly to systems, devices, and methods for monitoring signals such as forces and loads present on a toilet. Such systems, devices, and methods can provide accurate measures of a weight or ballistocardiogram (BCG) of an individual, which can be used to monitor certain physiological data or conditions of an individual and to inform the individual and/or healthcare providers of changes in such data or conditions necessitating certain therapies, treatments, lifestyle changes, etc.

Most individuals use toilets on a daily basis. Accordingly, health monitoring that can be conducted while an individual is seated on a toilet can provide an unobtrusive way of regularly monitoring information about that individual. Measures such as a seated weight or BCG of an individual seated on a toilet can be useful for monitoring certain conditions of the individual, such as, for example, a cardiac or vascular heath of the individual.

Systems and methods for monitoring seated individuals on toilets, however, can be inaccurate when certain loads and forces present on a toilet seat are not measured. For example, in conventional toilets, a ring (e.g., annular platform) of the toilet where an individual is typically seated is attached to a bowl or base of the toilet using a hinge. The ring can also be supported on the bowl by one or more bumpers (e.g. supports or legs) that make contact with a rim of the bowl. When loads or forces are transferred through the hinge and/or bumpers without being measured, this can lead to inaccurate measurements, e.g., in a weight or BCG of the individual. Accordingly, systems, devices, and methods described herein are design to measure loads and forces that are present at a hinge and/or bumper of a toilet seat.

Weight can be used to monitor and assess a number of conditions associated with an individual, including, for example, a surrogate body weight of a seated individual, a weight change due to defecation or urination, level of fluid retention, etc. Such conditions can be indicative of certain types of diseases, including, for example, heart failure and kidney failure. Dynamic forces on a toilet seat can also be indicative of characteristics associated with an individual's respiration, BCG, urination, defection, etc. In many instances, the magnitude of dynamic forces exerted by an individual on a toilet seat are small but important to accurately determine for various applications, including, for example, estimating stroke volume, cardiac output, weight of urination, weight of defection, respiration rate, etc.

Various sensing or monitoring systems can be used to measure loads or forces on a toilet. For example, in an embodiment, a toilet bowl can be placed on a weighing scale and the entire load on the toilet can be passed through a force sensor on the weighing scale. In another embodiment, a platform can be placed over a toilet bowl with no hinge coupling the platform to the toilet bowl. The platform can have legs similar to a chair that can carry loads and forces, and the legs can be placed on sensors and/or have integrated sensors to measure loads and forces. In yet another embodiment, a floating hinge (e.g., a hinge that bears no loads) can be used in combination with a toilet ring that has four bumpers or supports, which include sensors to measure loads and forces on the ring. Suitable example of floating hinges are described in U.S. Pat. No. 10,292,658, titled, "Apparatus, System, And Method For Mechanical Analysis Of Seated individual," issued May 21, 2019, which is incorporated herein by reference.

Certain sensing or monitoring systems for measuring loads, however, may not be practical to implement or use. For example, certain systems can be difficult to install or require an entire toilet to be replaced or modified to be able to integrate sensors into the toilet. Certain systems can be mechanically complex and impact robustness across a wide range of toilets. Given the wide range of toilet types (e.g., shapes, sizes, configurations), components of sensing and monitoring systems may be limited to select types of toilets. For systems where platforms or other components are being attached, such components may require additional space to accommodate and/or make it more difficult to clean or service a toilet. Systems including a floating hinge or other compliant and/or movable components can be unstable and allow for undesirable movement (e.g., while moving and/or sitting on a toilet ring or seat).

Systems, devices, and methods described herein address these limitations while providing accurate measurements of signals, such as loads or forces, present on a toilet. FIG. 1A is a schematic illustration of a sensing device 100 for monitoring signals present on a toilet (e.g., a lavatory), according to some embodiments. The device 100 can include one or more elements of a toilet, such as, for example, a ring 110, a coupler 120, one or more support(s) 130, a base 150, and a lid 160. In some embodiments, the device 100 can include each of these elements and can function as a standalone toilet. Alternatively, in some embodiments, the device 100 can include a subset of these elements and be integrated into a toilet (e.g., be installed on a toilet).

The ring 110 can be a component of a toilet on which a user or subject sits. The ring 110 can be positioned on top of the base 150, such that the ring 110 defines a centrally disposed opening therethrough, e.g., for receiving bodily fluids, defecation, etc. The shape and/or the dimensions of the ring 110 can be substantially similar or correspond to the shape and/or dimensions of a top portion of the base 150 (e.g., a top portion of a toilet bowl). For example, the shape of the ring 110 can be circular, oval, elliptical, and/or any other annular shape that generally matches or corresponds to the shape of the top portion of the base 150. In some embodiments, the shape of the ring 10 and/or one or more features and/or surface finishes of at least an outer surface of the ring 110 can be arranged to increase the ergonomics of the toilet to provide, for example, support and comfort to a user seated on the ring 110.

The ring 110 can be coupled to the base 150 via the coupler 120 and be supported on the base 150 by one or more support(s). The base 150 can be a base of a toilet, such as, for example, a bowl with a section for coupling to a floor. In some embodiments, the ring 110 can be movably coupled to the base 150, e.g., can pivot or translate relative to the base ISO. In some embodiments, the ring 110 can be fixed to the base 150 but can be removably coupled to the base 150, e.g., for cleaning and/or replacement purposes. Further details of the coupler 120 and the support(s) 130 are described below.

Optionally, the ring 110 can be operatively coupled to and/or include one or more sensor(s) 112. Sensor(s) 112, as described below, can be used to measure forces or loads present on the ring 110. In some embodiments, the ring 110 can include one or more structures that accommodate the sensor(s) 112. For example, the ring 110 can include a platform that is coupled to (e.g., supports) the one or more sensor(s) 112. The platform can be coupled to the rest of the ring 110 (e.g., a body of the ring 110), and the sensor(s) 112 can be configured to measure loads and/or forces that pass through the platform. In some embodiments, the platform can be removable and/or movable relative to the ring 110, e.g., to enable cleaning and/or maintenance of the sensor(s) 112 and/or other portions of the ring 110 or toilet. The sensor(s) 112 can be configured to measure one or more signals present on the ring 110. For example, the sensor(s) 112 can be configured to measure parameters that provide information regarding a weight or BCG of a seated individual, e.g., by accounting for static and/or dynamic loads or forces present on the ring 110 due to the weight of the individual. The sensor(s) 112 can be configured to measure changes in the parameters such as changes in loads and/or forces, which can be used to calculate, for example, a weight change due to defecation or urination. In some embodiments, information collected by the sensor(s) 112 can be used to determine the forces generated by a heart of the seated individual. In particular, as the heart forcefully ejects fluid into the aorta of the individual, the body of the individual undergoes a downward and upward force in a repeating pattern, which can cause changes in forces and/or loads exerted by the individual on the ring 110. The sensor(s) 112 can be configured to measure these changes and to provide BCG data for the individual over time.

In some embodiments, the sensor(s) 112 can be independent sensors configured to each measure changes in forces and loads exerted by the individual on the ring 110 and generate independent BCG data. This is in contrast to systems that use sensor bridges to capture the BCG waveform. The bridge configuration is used to increase the signal to noise ratio and sensitivity of the sensor. However, the use of a sensor bridge produces only one signal output for all sensors and does not allow for each sensor to be measured independently. Although the bridge configuration can increase the signal to noise ratio and sensitivity of the sensors allowing accurate BCG measurements under ideal circumstances (e.g., an individual standing upright on a scale while remaining still), it may not produce reliable measurement of BCG of a sitting individual, for example, on a toilet. That is to say, the individual's seated posture (as well motion artifacts) can impact the signal quality of the BCG and the waveform shape. In some embodiments, by measuring each sensor independently, the BCG data generated by each sensor 112 can be used by an algorithm to estimate the posture of the individual and extract a more accurate and reliable BCG. This not only can improve the BCG signal quality but can also make the measurement more repeatable.

In some instances, the BCG data can be measured from multiple sensors 112 and the static signal from each sensor can be used to determine the posture of the individual. For example, in some embodiments the ring 110 can include a first number of sensors 112 disposed on a front portion of the ring 110 (e.g., forward sensors) and a second number of sensors 112 disposed on the rear portion of the ring 110 (e.g., back sensors). Higher relative signals on the forward sensors is indicative of the subject leaning forward, with the ratio of the forward to back sensors indicative of the posture angle. In other instances, the subject height, weight, age and/or gender can be used in conjunction with the static signals described above for a more accurate determination of posture. In yet other instances, statistical analysis (e.g., machine learning) of signals gathered at different postures across a population can be used to provide a posture estimate from the obtained signals.

In some embodiments, the use of multiple independent sensor(s) 112 (e.g., four or more sensors 112) facilitates estimating the position of the seated individual as described above, which can assist in the accurate determination of the individual weight. As posture changes from an upright to leaning over position, more weight is carried by the feet to the floor. This is important for monitoring weight changes over time, especially for heart failure patients where rapid weight gain (water retention) is a predictive indicator of declining health.

The sensor(s) 112 can be coupled to a processor (e.g., an onboard processor and/or a processor of a separate compute device (see FIG. 2)) that can use the information collected by the sensor to evaluate various physiological data or conditions of the individual. For example, the forces measured by one or more sensor(s) 112 can be used to estimate information for the medical analysis of cardiac and vascular function of a seated individual, such as, for example, stroke volume, cardiac output, weight and/or speed of urination, weight and/or speed of defecation, respiration rate, and more. In some embodiments, data collected by a first type of sensor 112 (e.g., BCG data) can be combined with data produced by other sensor(s) 112, such as, for example, a photoplethysmography (PPG) sensor and/or electrocardiogram (ECG) sensor, to estimate relevant information for the medical analysis of cardiac and vascular function. Suitable examples of processing and/or evaluation of sensor data are described in U.S. Pat. No. 10,292,658, as incorporated by reference above.

Examples of sensor(s) 112 include load and/or force sensors, pressure sensors, ECG sensors, PPG sensors, light sensors, etc. In the case of load and/or force sensors, suitable examples of such sensors can include load cells (e.g., pneumatic load cells, hydraulic load cells, piezoelectric crystal load cells, inductive load cells, capacitive load cells, magnetostrictive load cells, strain gauge load cells), strain gages, force sensing resistors (FSR) or printed or flexible force sensors, optical force sensors, etc. With the information from the sensor(s) 112, a processor (e.g., onboard processor and/or a processor of a separate compute device (see FIG. 2)) can be used to determine one or more of the following information about an individual or subject: heart rate, heart rate variability, left ventricular ejection time, pre-ejection period, flow velocity, pulse transit time (e.g., based on ECG or BCG data), blood pressure, cardiac output, cardiac contractility, abnormal heart function, blood oxygenation levels (e.g., $SpO_2$), respiration rate, stress levels (e.g., via heart rate variability), body weight, cardiac waveform characteristics (e.g., magnitudes and/or intervals), etc.

Posture information estimated from BCG data can also be used to determine temporal segments for specific BCG analysis where the subject has consistent posture. Aortic valve opening is then determined from a combination of the dynamic BCG signal and the subject posture. For example, in some embodiments the specific BCG waveform feature to be extracted is posture dependent. In an upright posture, aortic valve opening can be associated with the first upward peak of the BCG waveform from the beginning of the cardiac cycle. In a leaning forward position, aortic valve opening can be associated with the first downward peak of the BCG waveform from the beginning of the cardiac cycle.

The device 100 can include one or more support(s) 130. The support(s) 130 can be, for example, bumpers. As described above, the support(s) 130 can be configured to support the ring 110 on the top portion of the base 150 (e.g., a top portion of a toilet bowl). The support(s) 130 can have the shape of a square, a circle, and ellipse, or any other suitable geometrical shape for engaging a surface of the base 150. In some embodiments, a support 130 can have an elongated shape that extends along an annular portion of the ring 110. For example, a single support 130 can be used in some embodiments, where the support extends along a front portion of the ring 110. In some embodiments, the support(s) 130 can be integrated to the ring 110, while in other embodiments, the support(s) 130 can be removably attached to the ring 110. The support(s) 130 can be coupled to the ring (110) using various coupling mechanisms including, but not limited to, bolt fasteners, welding, brazing, adhesives, or any combination thereof.

In some embodiments, the support(s) 130 can optionally include one or more sensor(s) 132. The sensor(s) 132 can be disposed within the support(s) 130 and/or be disposed on a surface of the support(s) 130. The sensor(s) 132 can be structurally and/or functionally similar to the sensor(s) 112. For example, the sensor(s) 132 can be configured to measure one or more parameters, e.g., forces and/or loads, BCG data, posture, etc. The sensor(s) 132, collectively with sensor(s) 112, 122 described herein, can be configured to measure one or more parameters such that information about an individual or subject seated on the device 100 can be accurately determined (e.g., weight, BCG, posture, etc.).

In some embodiments, each support 130 can include a sensor 132. Alternatively, some support(s) 130 can include sensor(s) 132 while others do not include sensor(s) 132. In some embodiments, at least one support 130 can include a sensor that is different from another support 130. In some embodiments, at least one support 130 can include a plurality of sensor(s) 132, e.g., for measuring different physiological data or conditions.

In some embodiments, the ring 110 and the support(s) 130 each can include sensor(s) (e.g., sensor(s) 112, 132). In some embodiments, the ring 110 can include sensor(s) 112, while the support(s) 130 do not include sensors. For example, the ring 110 can include sensor(s) 112 for sensing a load and/or force at a coupling or interface between the ring 110 and the support(s) 130. Alternatively, in some embodiments, the support(s) 130 can include sensor(s) 132, while the ring 110 does not include any sensors. In some embodiments, the support(s) 130 and their respective sensor(s) can be disposed symmetrically about a central longitudinal axis of the ring 110. In some embodiments, the support(s) 130 and their respective sensor(s) can be located towards the front of the ring 110, which corresponds to the front of the base 150. In some embodiments, the support(s) 130 and their respective sensor(s) can be located at locations other than the front of the ring 110, e.g., towards the sides or the rear portion of the ring 110.

As described above, the ring 110 can be coupled via the coupler 120 to the base 150. The coupler can be a hinge of a toilet. The coupler 120 can be located towards the back of the base 150 and can secure the ring 110 and/or the lid 160 to the base 150. The coupler 120 can allow for movement of the ring 110 and/or lid 160 relative to the base 150, e.g., to allow access to portions of the base 150, the ring 110, and/or lid 160 for cleaning purposes.

In some embodiments, the coupler 120 can optionally include one or more sensor(s) 122. The sensor(s) 122 can be disposed within the coupler 120 and/or be disposed on a surface of the coupler 120. In some embodiments, the sensor(s) 122 can be disposed on a platform that is coupled to and/or integrated into the coupler 120. The sensor(s) 122 can be structurally and/or functionally similar to the sensor(s) 112, 132. For example, the sensor(s) 122 can be configured to measure one or more characteristics or conditions, e.g., forces and/or loads, BCG data, etc. The sensor(s) 122, collectively with sensor(s) 112, 132 described herein, can be configured to measure one or more parameters such that information about an individual or subject seated on the device 100 can be accurately determined (e.g., weight, BCG, etc.).

The lid 160 can be a lid of a toilet. In some embodiments, the lid 160 can be coupled to the ring 110 and/or base 150 via the coupler 120. The lid 160 can be configured to cover an opening of the ring 110. In some embodiments, the shape and/or the dimensions of the lid 160 can be substantially similar to the shape and/or dimensions of a top portion of the base 150 (e.g., a top portion of a toilet bowl).

In some instances, a user can lower the lid 160 of the toilet and sit on the lid 160 to provide information to one or more sensors located on or coupled to the lid 160. For example, the lid 160 can optionally include one or more sensor(s) 162 that are structurally and/or functionally similar to sensor(s) 112. Sensor(s) 162 can be configured to measure one or more signals present on the lid 160. In an embodiment, sensor(s) 162 can be configured to measure parameters that provide information regarding a weight, BCG, or posture of a seated individual, e.g., by accounting for static and/or dynamic loads or forces present on the lid 160 due to the weight of the individual. The sensor(s) 162 can be coupled to a processor (e.g., an onboard processor and/or a processor of a separate compute device (see FIG. 2)) that can use the information collected by the sensor to evaluate various physiological data or conditions of the individual In some embodiments, the base 150 can optionally include one or more sensor(s) 152. The sensor(s) 152 can be disposed on a surface of the base directly underneath the positions where the support(s) 130 contact the base 150. In some embodiments, each sensor(s) 152 can be disposed on a platform that is coupled to and/or integrated into the base 150, such that the sensors(s) 152 are located at the positions where the supports(s) 130 contact the base. The sensor(s) 152 can be structurally and/or functionally similar to the sensor(s) 112, 132. For example, the sensor(s) 122 can be configured to measure one or more characteristics or conditions, e.g., forces and/or loads, BCG data, etc. The sensor(s) 122, collectively with sensor(s) 112, 132, and 162 described herein, can be configured to measure one or more parameters such that information about an individual or subject seated on the device 100 can be accurately determined (e.g., weight, BCG, posture, etc.).

The sensor(s) 112, 122, 132, 152, and 162 can be distributed about a seating area of an individual (e.g., the ring 110, the base 150, or lid 160), such that the sensor(s) 112, 122, 132, 152, and 162 can collectively measure loads and/or forces present on the ring 110, the base 150, or lid 160 due to a weight of the seated individual. Each of the sensor(s) 112, 122, 132, 152, 162 can be independent sensors that monitor changes in loads and/or forces and provide independent signals for analysis. The independent signals provided by the sensors can be used to reduce noise (e.g., by averaging or comparing the independent signals) and/or provide a more accurate measure of weight, BCG, posture of the seated individual, and other physiological characteristics or conditions. The sensor(s) 112, 122, 132, 152, 162 can be positioned at each point of transfer (e.g., points of contact or coupling) between the ring 110 and the base 150 or the lid 160 and the ring 110 and/or base 150 such that substantially all loads and/or forces exerted on the ring 110 or lid 160 by the seated individual are measured by the sensor(s) 112, 122, 132, 152, 162. Therefore, collectively, the sensor(s) 112, 122, 132, 152, 162 can ensure accurate capture of weight, BCG, and other physiological characteristics or conditions of the individual without losing signal to any transfer points.

In an embodiment, a toilet can include at least three points of contact between a ring 110 and a base 150. Sensors (e.g., sensor(s) 112, 122, 132, or 162) can be disposed at these points of contact to measure loads or forces. For example, a ring 110 can include two supports 130 at or near its front end. Each support 130 can represent one point of contact between the ring 110 and the base 150, and therefore sensors can be disposed at each of the supports 130, e.g., within each support 130 or within the ring 110. The ring 110 can be coupled to a base 150 at its back end via a coupler 120. The coupling point between the ring 110 and the base 150 via the coupler 120 can represent a third point of contact, and therefore a sensor can be disposed at this coupling point. e.g., within the ring 110 or within the coupler 120. In another example, a lid 160 can include two supports or bumpers near a front end, and each support can represent one point of contact between the lid 160 and a ring 110 and/or base 150. The coupling point between the lid 160 and the base 150 via the coupler 120 can represent a third point of contact. Sensors disposed at each of these points can then measure signals present on the lid 160. By having three points of contact and sensors disposed accordingly to measure load or forces at these points, the device 100 can measure total or entire loads or forces present within a plane defined by the three points. Additional points of contact can be included (e.g., by having additional sensors), which can further collect load or force data, and be used to account for noise and/or error in the sensor data.

Figure 1B:
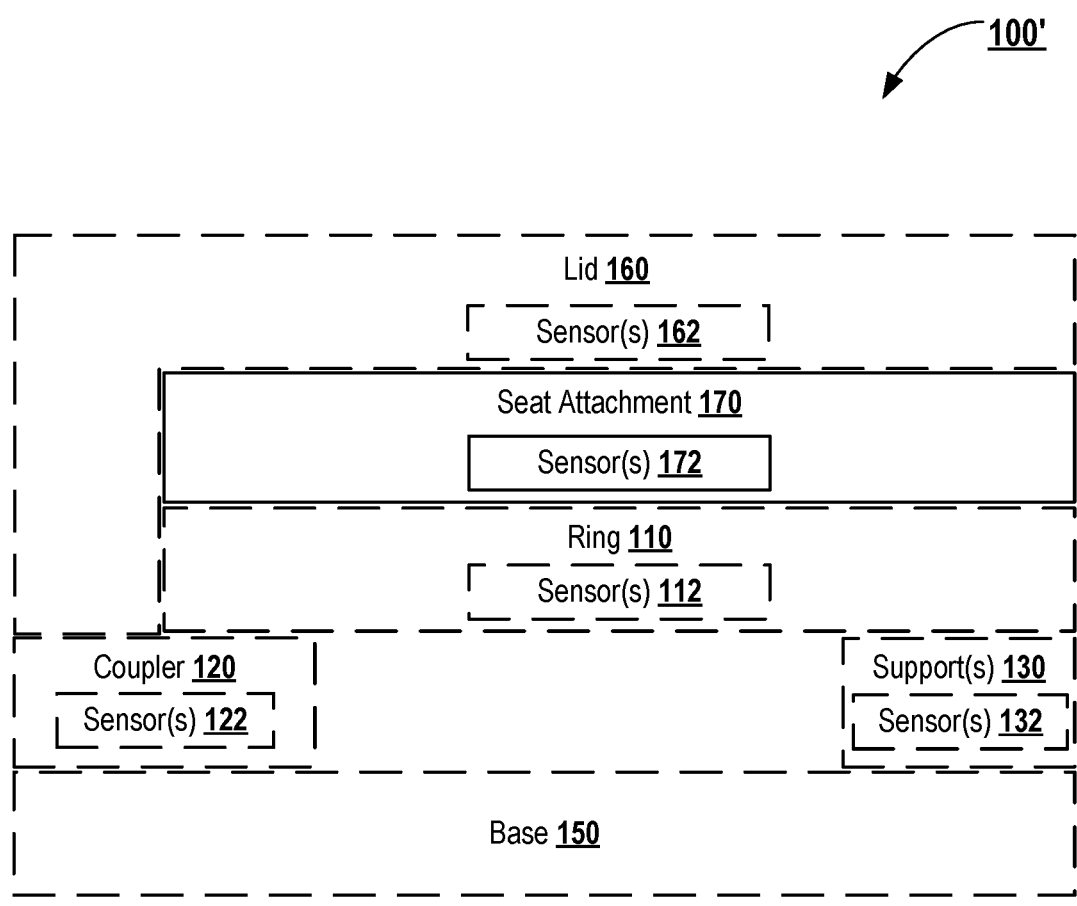
FIG. 1B is a schematic illustration of a device for monitoring signals (e.g., loads or forces) present on a toilet, according to an embodiment.

FIG. 1B shows a schematic illustration of another example device 100' for monitoring load and forces on a toilet (e.g., lavatory), according to some embodiments. The device 100' can include components that are structurally and/or functionally similar to the device 100. For example, the device 100' can optionally include one or more of a ring 110, a coupler 120, a support 130, a base 150, and a lid 160.

Additionally or alternatively, the device 100' can include a seat attachment 170. The seat attachment 170 can be configured to attach to a ring or a base of a toilet (e.g., ring 110 or base 150). For example, the seat attachment 170 can be a seat replacement that attaches to a bowl of a toilet. Alternatively, the seat attachment 170 can be a seat cover or extension that attaches to a ring of a toilet. The seat attachment 170 can have an annular shape and include an opening, e.g., similar to a ring of a toilet.

The seat attachment 170 can include one or more sensor(s) 172. The sensor(s) 172 can be disposed within the seat attachment 170 and/or disposed on a surface of the seat attachment 170. In some embodiments, the seat attachment 170 can include one or more structures (e.g., compartments, bumpers, etc.) that can house the sensor(s) 172. The sensor(s) 172 can be structurally and/or functionally similar to the sensor(s) 112, 122, 132, as described with reference to FIG. 1. For example, the sensor(s) 172 can be configured to measure one or more parameters, e.g., forces and/or loads, BCG data, etc. In some embodiments, the sensor(s) 172 can include a plurality of sensors 172 that are distributed about the seat attachment 170 such that the sensors can measure forces and/or loads around the seat attachment 170 when an individual or subject is seated on the seat attachment 170. In some embodiments, a single sensor 172 extending around the seat attachment 170 (or at least extending partially around the seat attachment 170) can be used to measure forces and/or loads present on the seat attachment 170. In some embodiments, the device 100' can include other components, e.g., a ring 110 and/or a coupler 120, that also includes sensor(s) (e.g., sensor(s) 112, 122) that can operate together with sensor(s) 172 to provide information about various parameters, e.g., forces and/or loads, BCG, etc. In some embodiments, the other components of the device 100', e.g., ring 110 and/or coupler 120, may not include any sensors, such that all the sensors are integrated into or coupled to the seat attachment 170. In some embodiments, the seat attachment 170 may not include any sensor(s) 172 and the sensors may be included in the other components of the device 100', e.g., the ring 110 and/or coupler 120.

Figure 2:
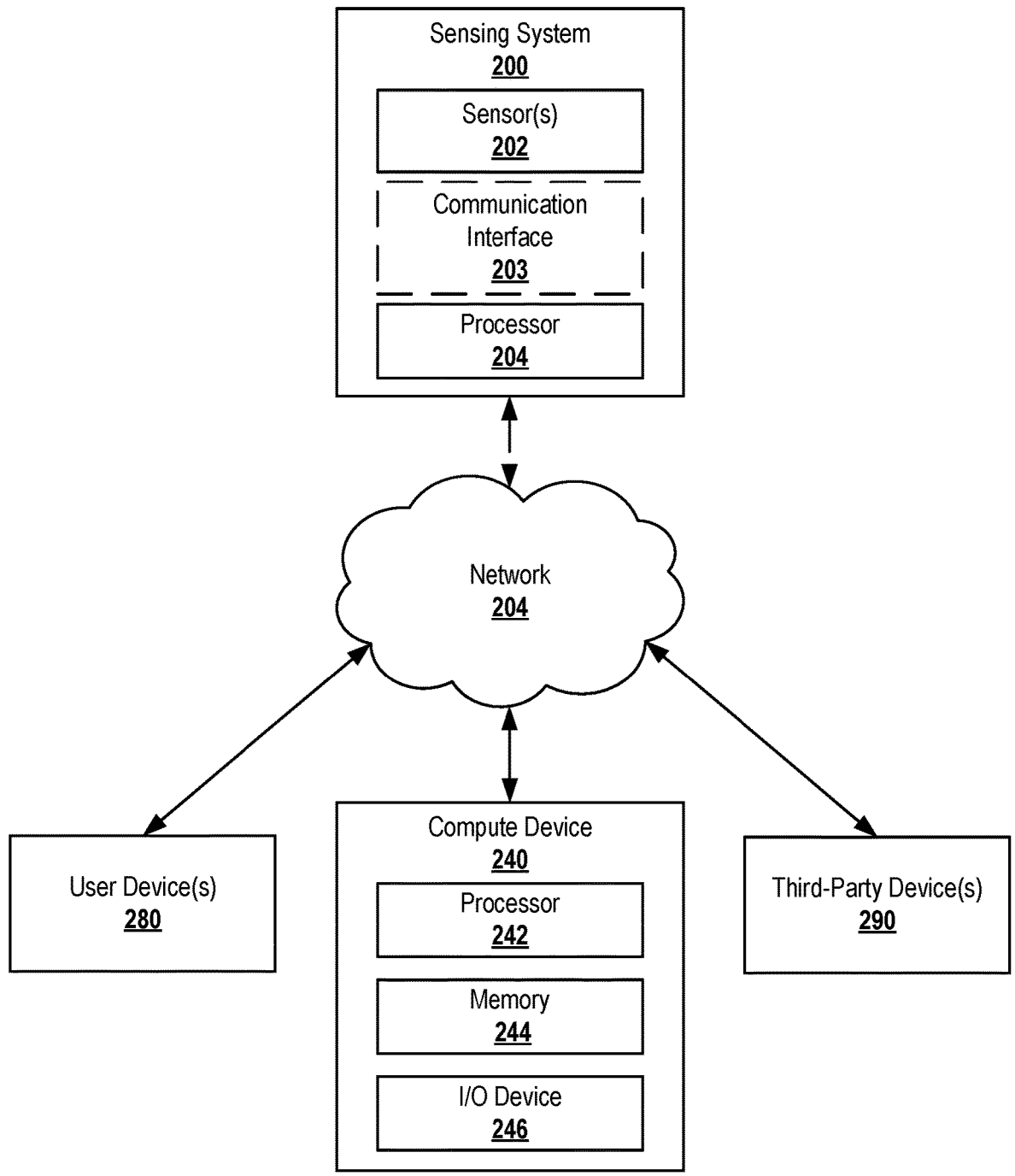
FIG. 2 schematically depicts a network of devices for monitoring physiological conditions of a subject, according to an embodiment.

FIG. 2 depicts a block diagram illustrating a sensing system 200 in communication with other devices via a network 204. In some embodiments, sensing system 200 can be configured to measure physiological data or conditions present on a toilet, such as, for example, loads or forces. Sensing system 200 can include component(s) that are structurally and/or functionally similar to those of other sensing systems and devices described herein, including, for example, device 100. For example, sensing system 200 can include one or more sensor(s) 202 that can be configured to measure loads or forces. Sensor(s) 202 can be disposed about a ring (e.g., ring 110) of a toilet to collect sensor data representative of loads or forces exerted on the ring by an individual seated on the ring. In an embodiment, at least three sensors 202 can be disposed about the ring to measure total loads and forces present on the ring. The three sensors 202 can be positioned at three contact points between the ring and a base of the toilet (e.g., a base 150).

Sensing system 200 can communicate with a compute device 240, one or more user device(s) 280, one or more third-party device(s) 290, etc. via a network 204. The network 204 can include one or more network(s) that may be any type of network (e.g., a local area network (LAN), a wide area network (WAN), a virtual network, a telecommunications network) implemented as a wired network and/or wireless network and used to operatively couple to any compute device, including sensing system 200, compute device 240, user device(s) 284), and third-party device(s) 290.

Optionally, sensing system 200 can be configured to send data measured by sensor(s) 202 via a communication interface 203 to the compute device 240, one or more user device(s) 280, and/or one or more third-party device(s) 290. In some embodiments, sensing system 200 can include onboard processing, such as, for example, a processor 204 implemented as a microprocessor, to process sensor data (e.g., filter, convert, etc.) prior to sending the sensor data to the compute device 240, one or more user device(s) 280, and/or one or more third-party device(s) 290. Alternatively, sensing system 200 can be configured to send raw sensor data to the compute device 240, one or more user device(s) 280, and/or one or more third-party device(s) 290. In some embodiments, processor 204 can be configured to analyze the sensor data and/or determine information such as weight, BCG, or other physiological data or conditions of a subject (e.g., an individual seated on a toilet). In some embodiments, processor 204 can be configured to present this information to a user, e.g., via an onboard display, audio device, or other output device. In some embodiments, the processor 204 can interface with the communication interface 203 to transmit information to an external device. The communication interface 203 can be configured to allow two-way communication with the external device, including, for example, the compute device 240, one or more user device(s) 280, and/or one or more third-party device(s) 290. The communication interface 203 can include a wired or wireless interface for communicating over the network 204.

The compute device 240 can be configured to process and/or analyze the sensor data, e.g., received from the sensor(s) 202. In some embodiments, the compute device 240 can be a nearby compute device (e.g., a local computer, laptop, mobile device, tablet, etc.) that includes software and/or hardware for receiving the sensor data and processing and/or analyzing the sensor data. In some embodiments, the compute device 240 can be a server that is remote from the sensing system 200 but can communicate with the sensing system 200 via network 204 and/or via another device on the network 204 (e.g., a user device 280). For example, sensing system 200 can be configured to transmit sensor data to a nearby device (e.g., a user device 280), e.g., via a wireless network (e.g., Wi-Fi, Bluetooth®, Bluetooth® low energy, Zigbee and the like), and then that device can be configured to transmit the sensor data to the compute device 240 for further processing and/or analysis.

The user device(s) 280 can be compute device(s) that are associated with a user of a toilet equipped with the sensing system 200. Examples of user device(s) 280 can include a mobile phone or other portable device, a tablet, a laptop, a personal computer, a smart device, etc.). In some embodiments, a user device 280 can receive sensor data from the sensing system 200 and process that sensor data before passing the sensor data to the compute device 240. For example, a user device 280 can be configured to reduce noise (e.g., filter, time average, etc.) raw sensor data. In some embodiments, a user device 280 can be configured to analyze the sensor data and present (e.g., via a display) information representative of or summarizing the sensor data. In some embodiments, a user device 280 can provide weight information, heart rate information, etc. to a user. In some embodiments, a user device 280 can transmit the sensor data to the compute device 240, which can analyze the sensor data and send information representative of or summarizing the sensor data back to the user device 280 for presenting (e.g., via a display) to a user.

The third-party device(s) 290 can be compute device(s) associated with other individuals or entities that have requested and/or been provided access to a user's data. For example, the third-party device(s) 290 can be associated with healthcare professionals (e.g., physicians, nurses, therapists) and/or caregivers of the user. The user can select to have certain third parties have access to the user's health data (e.g., including health data obtained from sensor data collected by sensing system 200). The third parties can then track the user's health information to determine whether the user is at risk for certain conditions and/or needs certain interventions, treatments, or care.

The compute device 240 can include a processor 242, a memory 244, and an input/out device (WO) 246 (or a multiplicity of such components). The memory 244 can be, for example, a random access memory (RAM), a memory buffer, a hard drive, a database, an erasable programmable read-only memory (EPROM), an electrically erasable read-only memory (EEPROM), a read-only memory (ROM), and/or so forth. In some embodiments, the memory 244 stores instructions that cause processor 242 to execute modules, processes, and/or functions associated with processing and/or analyzing sensor data from sensing system 200.

The processor 242 of compute device 240 can be any suitable processing device configured to run and/or execute functions associated with processing and/or analyzing sensor data from sensing system 200. For example, processor 242 can be configured to process and/or analyze sensor data (e.g., received from sensor(s) 202), to determine a weight, BCG, or other physiological data or conditions of an individual. The processor 242 can be a general purpose processor, a Field Programmable Gate Array (FPGA), an Application Specific Integrated Circuit (ASIC), a Digital Signal Processor (DSP), and/or the like.

The I/O device 246 of the compute device 240 can include one or more components (e.g. a communication or network interface) for receiving information and/or sending information to other devices (e.g., sensing system 200, user device(s) 280, third-party device(s) 290). In some embodiments, the I/O device 246 can optionally include or be operatively coupled to a display, audio device, or other output device for presenting information to a user. In some embodiments, the I/O device 246 can optionally include or be operatively coupled to a touchscreen, a keyboard, or other input device or receiving information from a user.

Figure 3A:
FIGS. 3A, 3B, and 3C are schematic diagrams depicting different kits of components for monitoring signals (e.g., loads or forces) present on a toilet according to embodiments.
Figure 3B:
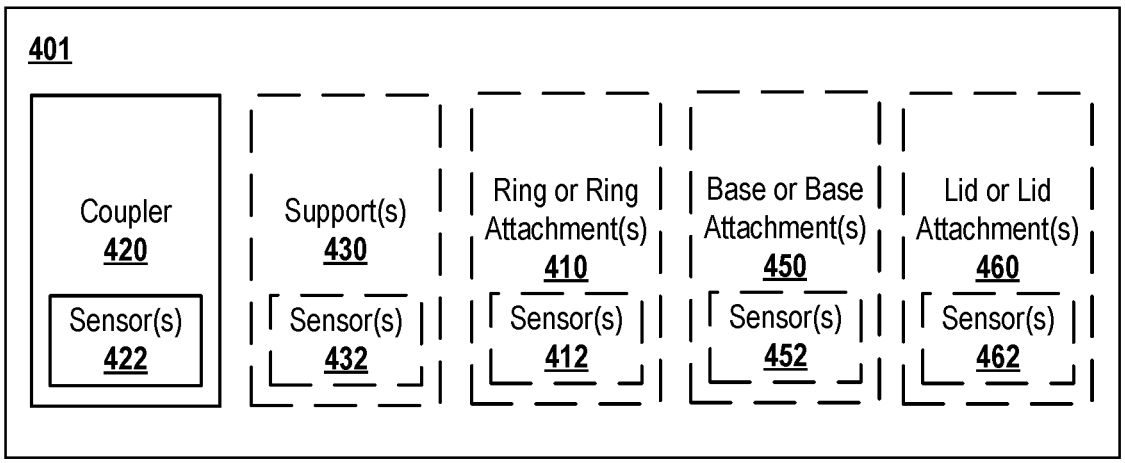
Figure 3C:
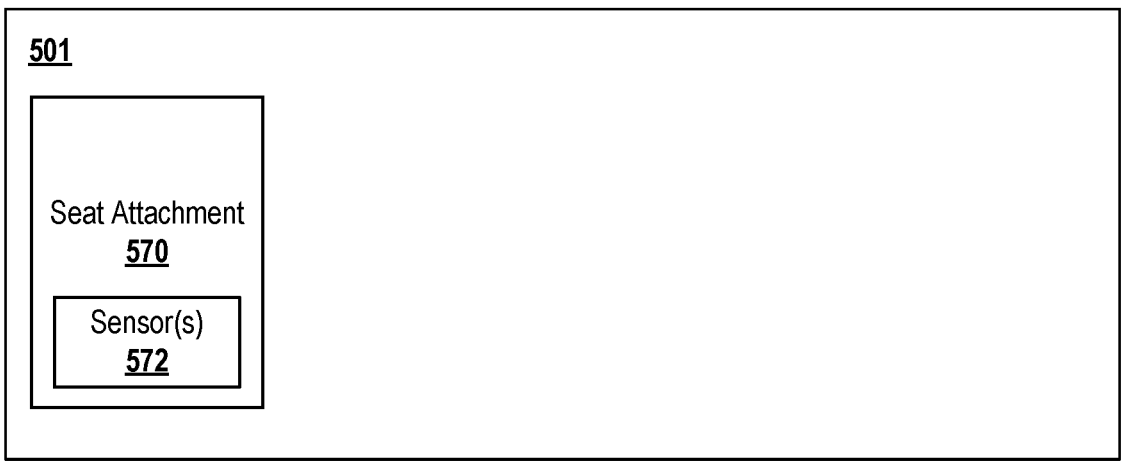

FIGS. 3A-3C schematically depict different components of a sensing device or system, e.g., such as those as described with reference to FIGS. 1A, 1B, and 2. The components of the sensing device can be provided, for example, in various kits 301, 401, 501, each including a different combination of components. In some embodiments, the kits 301, 401, 501 can be provided to enable a user to modify (e.g., retrofit) a toilet to have sensing functionality, as described herein. In some embodiments, the kits 301, 401, 501 can be provided as part of or for incorporation into a larger kit for installing a new toilet that has sensing functionality.

FIG. 3A an example kit 301. The kit 301 can include a ring 310. The ring 310 can be structurally and/or functionally similar to the ring 110 described with reference to FIG. 1A. For example, the ring 310 can include a set of sensor(s) 312. After the ring 310 is installed on a toilet (e.g., using a coupler), the sensor(s) 312 of the ring 310 can be configured to measure loads and/or forces present on the ring 310, e.g., when an individual is seated on the ring 310, and such loads and/or forces can be transmitted to a processor (e.g., of a user device 280 and/or a compute device 240) for processing and/or analysis. A user with kit 301 can modify an existing toilet to have sensing functionality by replacing a ring of the toilet with ring 310 (e.g., removing the existing ring of the toilet and installing the ring 310). Alternatively, the ring 310 can be provided with other components for installing a new toilet and be installed as the seat in the new toilet.

FIG. 3B depicts an example kit 401. The kit 401 can include a coupler 420, such as, for example, a hinge or other component for coupling a lid and/or a ring to a toilet. The coupler 420 can be structurally and/or functionally similar to the coupler 120 describe with reference to FIG. 1A. For example, the coupler 420 can include a set of sensor(s) 422. The set of sensor(s) 422 can include a sensor that is configured to measure loads and/or forces present on a ring of a toilet, e.g., when an individual is seated on the ring. The sensor(s) 422 can be configured to measure the loads and/or forces that are transferred from the ring of the toilet through the coupler 420 to a base (e.g., bowl) of the toilet. The sensor(s) 422, together with other sensors that are present around the ring and/or base of the toilet, can measure total or entire force exerted by a seated individual on the toilet, such that the sensors can collectively provide force data that can be used to measure physiological data of the seated individual (e.g., weight, BCG, etc.).

In some embodiments, the kit 401 can optionally include support(s) 430 (e.g., bumpers) including sensor(s) 432 for installing on other parts of a ring of a toilet. For example, the kit 401 can include at least two supports 430 that are installed around the ring, and together with the coupler 420, the supports 430 and the coupler 420 via their sensors 422, 432 can be configured to measure loads and/or forces present on the ring. Alternatively or additionally, the kit 401 can optionally include a ring or ring attachment 410 (e.g., supports or bumpers that attach to a ring) that can include sensor(s) 412. Alternatively or additionally, the kit 401 can include a base or base attachment 450 (e.g., a platform that can attach to the base) that can include sensor(s) 452. Alternatively or additionally, the kit 401 can optionally include a lid or lid attachment 460 (e.g., supports or bumpers that attach to a lid) that can include sensor(s) 462. These various components can be installed together to provide a toilet that has sensing functionality. A user with kit 401 can modify an existing toilet to have sensing functionality by removing existing components of the toilet (e.g., a coupler or hinge, a ring, a ring support or bumper, a base, a lid) and installing one or more of the coupler 420, support(s) 430, ring or ring attachment 410, base or base attachment 450, or lid or lid attachment 460. Alternatively, a new toilet can be installed with one of more of the coupler 420, support(s) 430, ring or ring attachment(s) 410, base or base attachment(s) 450, or lid or lid attachment 460.

FIG. 3C depicts an example kit 501. The kit 501 can include a seat attachment 570, such as, for example, a cover, platform, or other structure for positioning on top of a bowl or a ring of a toilet. The seat attachment 570 can be structurally and/or functionally similar to the seat attachment 170 described with reference to FIG. 1B. For example, the seat attachment 570 can include a set of sensor(s) 572. Ater the seat attachment 570 is installed on a toilet, the sensor(s) 572 of the seat attachment 570 can be configured to measure loads and/or forces present on the seat attachment 570, e.g., when an individual is seated on the seat attachment 570, and such loads and/or forces can be transmitted to a processor (e.g., of a user device 280 and/or a compute device 240) for processing and/or analysis. In some embodiments, the seat attachment 570 can be portable such that a user can move the seat attachment 570 between different toilets to modify those toilets to have sensing functionality.

Figure 4:
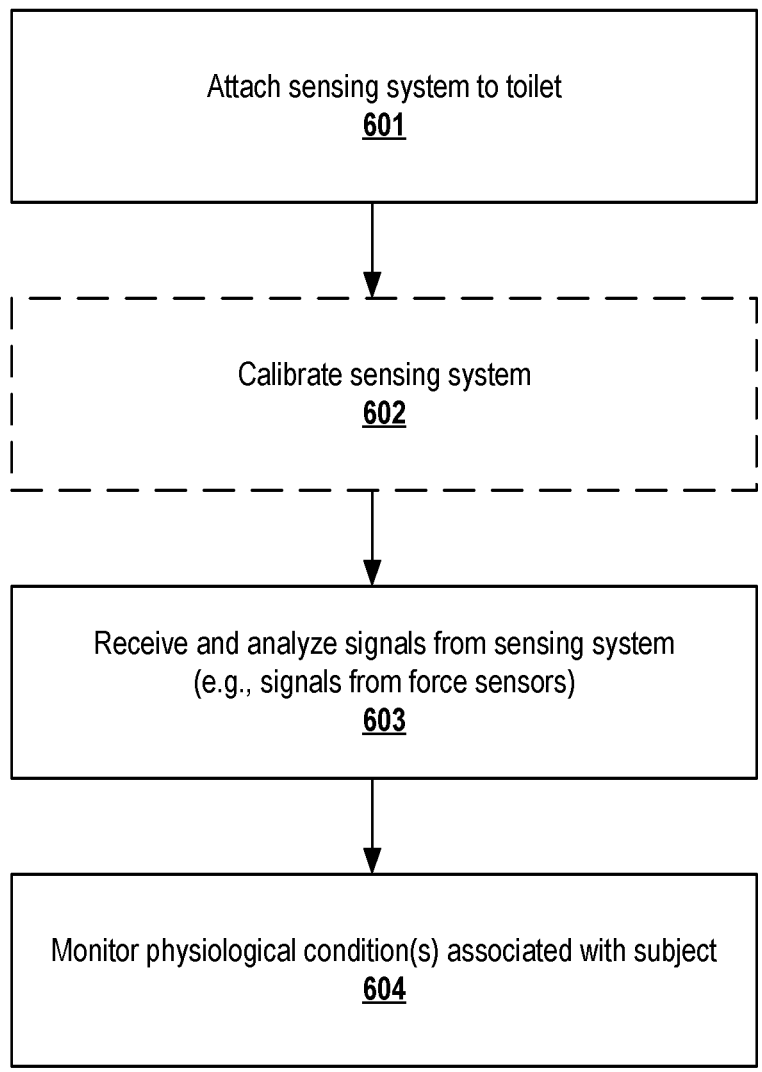
FIG. 4 is a flow chart of an example method of operating a device for monitoring signals (e.g., loads or forces) present on a toilet according to an embodiment.

FIG. 4 depicts an example method 600 of using systems and devices described herein. A user can attach or install a sensing system or device (e.g., 100, 100', 200, etc.) onto a toilet, at 601. The system can then be calibrated, at 602, e.g., by allowing one or more sensors (e.g., sensors 112, 122, 132, 202, 312, 412, 422, 432, 452, 572) of the sensing system to collect data and send that data to a processor (e.g., onboard processor and/or processor associated with an external compute device (e.g., user device 280, compute device 240)) and having the processor calibrate the sensing system. In some instances, the system can be calibrated by first collecting data while a user is not seated on the toilet, and then collecting data while the user is seated on the toilet. In some embodiments, the system can be calibrated during manufacturing. In some embodiments, the system can be calibrated during or after installation of the system, e.g., to account for different attachments of the system components to a toilet. In some embodiments, the system can be calibrated to a particular user.

Signals can be received from the sensing system (e.g., load and/or force data from one or more force sensors) and processed and/or analyzed by a processor (e.g., onboard processor and/or processor associated with an external compute device (e.g., user device 280, compute device 240)), at 603. The signals can be received when a user is seated on the toilet, such that the signals can be indicative of various physiological data of the user. Based on the signals received from the sensing system, the processor can then monitor one or more physiological condition(s) associated with the user, at 604. Optionally, the processor can present information of the monitored data to a user and/or provide feedback to a user based on the monitored data, such as through one or more compute devices (e.g., user device 280, compute device 240, and/or third-party device 290).

Figure 5:
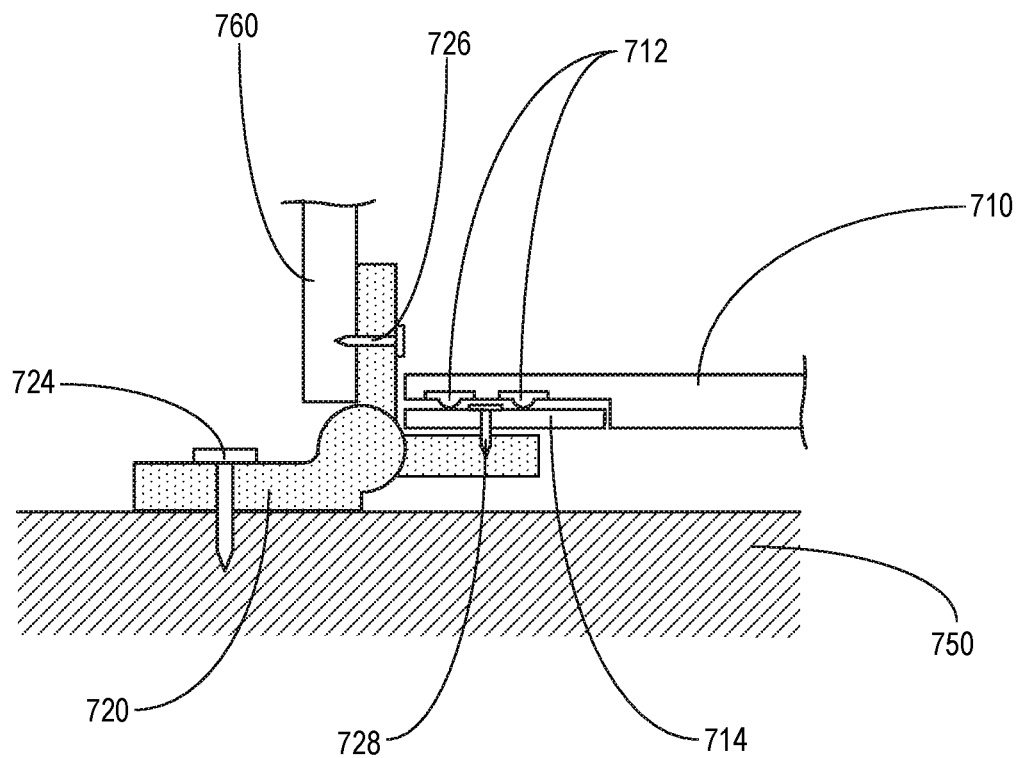
FIG. 5 depicts a side view of a portion of a toilet including components for monitoring one or more loads or forces present on the toilet according to an embodiment.

FIG. 5 shows a schematic illustration of a portion of a toilet including a sensing device 700 for monitoring signals present on the toilet, according to some embodiments. The device 700 can include components that are structurally and/or functionally similar to other sensing devices and/or systems described herein, including, for example, the devices 100 or 100' described above with reference to FIGS. 1A and 1B.

The device 700 can include a ring 710, which interfaces with one or more other components of the toilet. For example, the ring 710 can be installed on the toilet using a coupler 720 (e.g., a hinge). The coupler 720 can couple the ring 710 to a base 750 of the toilet. The coupler 720 can also couple a lid 760 of the toilet to the base 750. As shown in FIG. 5, the coupler 720 and the ring 710 can be attached to one another using a bolt 728. Other or additional attachment mechanisms, however, can be used, including, for example, a fastener, a screw, welding, brazing, an adhesive, or any combination thereof. Similarly, the coupler 720 and the lid 760 can be attached to one another using a bolt 726 and/or other suitable attachment mechanism, and the coupler 720 and the base 750 can be attached to one another using a bolt 724 and/or other suitable attachment mechanism. In some embodiments, the coupler 720 can be implemented as a hinge and can allow the lid 760 and the ring 710 to pivot relative to each other and the base 750. In some embodiments, one or both of the lid 760 and/or ring 710 can be integrally formed with a portion of the coupler 720.

The ring 710 can function similarly to a ring of a standard toilet, but be configured with additional sensing components. For example, the ring 710 can include a set of sensors, including sensor(s) 712. The sensor(s) 712 can be disposed at or near a portion of the ring 710 that is attached to the coupler 720, such as, for example, a rear portion of the ring 710. The sensor(s) 712 can be configured to measure signals present on the ring 710 that are transferred through the coupling point between the ring 710 and the coupler 720.

In some embodiments, the ring 710 can include an internal platform 714. The platform 714 can be disposed at the rear portion of the ring 710, where the ring 710 is attached to the coupler 720. The platform 714 can be connected to one or more other sections of the ring 710. The sensor(s) 712 can be located adjacent to the platform 714, as shown in FIG. 5. In some embodiments, one or more sensor(s) 712 can be disposed on a surface of the platform 714. Alternatively or additionally, the sensor(s) 712 can be disposed on an internal surface of the ring 710 opposite the platform 714. The sensor(s) 712 can be structurally and/or functionally similar to the sensor(s) 112. For example, the sensor(s) 712 can be configured to measure one or more signals, e.g., forces and/or loads, etc.

While not depicted in the partial view of the toilet in FIG. 5, the ring 710 can also include one or more support(s) (e.g., bumpers or legs, such as, for example, support(s) 130) with one or more sensor(s). The sensor(s) at the supports can also be configured to measure one or more signals, e.g., forces and/or loads, etc. In some embodiments, the sensor(s) 712, collectively with sensor(s) at the support(s), can be configured to measure total or entire forces and/or loads present on the ring 710, such that physiological data (e.g., weight, BCG, etc.) of a user seated on the ring 110 can be determined.

Figure 6:
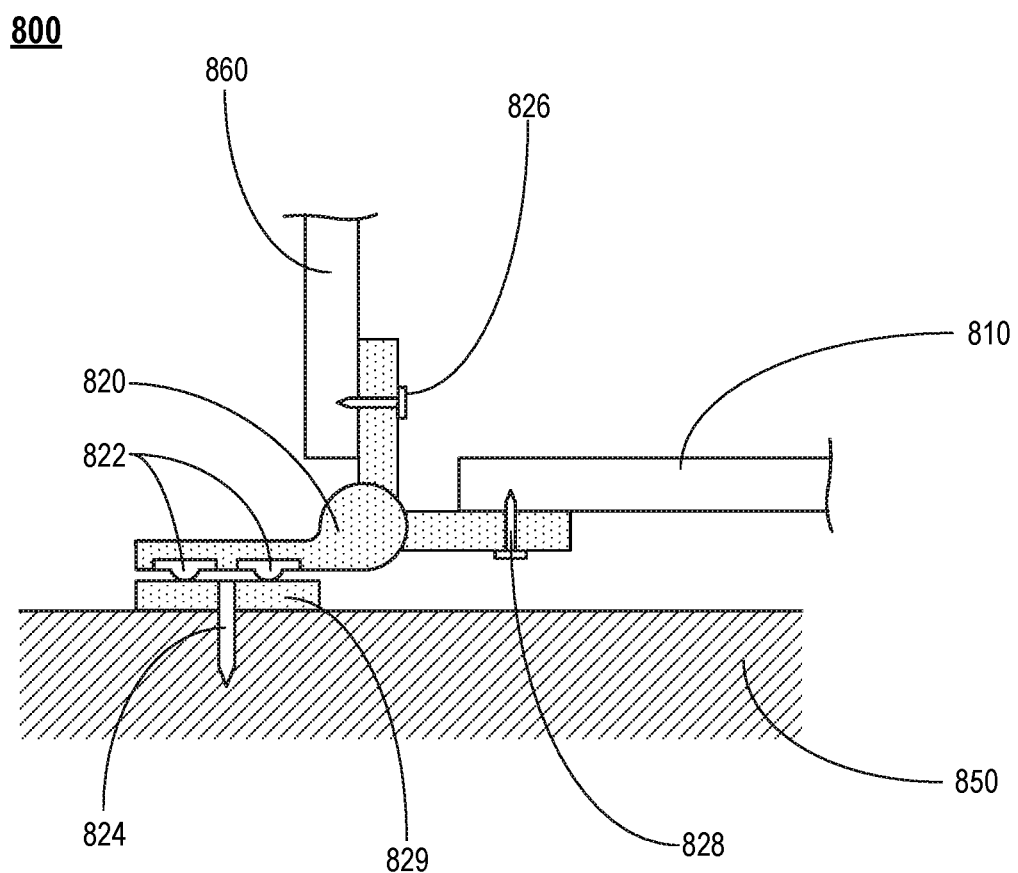
FIG. 6 depicts a side view of a portion of a toilet including components for monitoring one or more loads or forces on the toilet according to an embodiment.

FIG. 6 shows a schematic illustration of a portion of a toilet including a sensing device 80X) for monitoring signals, such as loads and/or forces, on the toilet, according to some embodiments. The device 800 can include components that are structurally and/or functionally similar to other sensing devices and/or systems described herein, including, for example, the devices 100 or 100' described above with reference to FIGS. 1A and 1B.

The device 800 can include a coupler 820, which can interface with one or more other components of the toilet. For example, the coupler 820 can be installed on the toilet and be used to couple a ring 810 and a lid 860 to a base 850 (e.g., bowl) of the toilet. The coupler 820 can be attached to the ring 810, lid 860, and base 854) using bolts 828, 826, 824, respectively, and/or other suitable attachment mechanisms (e.g., a fastener, a screw, welding, brazing, an adhesive, or any combination thereof). The coupler 820 can allow the ring 810 and the lid 860 to pivot relative to one another and to the base 850. The coupler 820 can function similarly to a hinge of a standard toilet, but be configured with additional sensing components. For example, the coupler 820 can include a set of sensors, including sensor(s) 822. The sensor(s) 822 located on the coupler 820 can be configured to capture signals such as forces and/or loads transferred to the coupler 820 from an individual or subject seated on the device 800.

In some embodiments, the coupler 820 can include an internal platform 829. The platform 829 can be disposed at a coupling between the coupler 820 and the base 850. Alternatively, the platform 829 can be disposed at a coupling between the coupler 820 and the ring 810. In some embodiments, the coupler 820 can include multiple platforms 829 disposed at different coupling points, e.g., between the ring 810 and the coupler 820, or between the base 850 and the coupler 820.

The platform 829 can be connected to one or more other sections of the coupler 820 (e.g., a body of the coupler 820). The sensor(s) 822 can be located adjacent to the platform 829, as shown in FIG. 6. In some embodiments, one or more sensor(s) 822 can be disposed on a surface of or integrated in the platform 829. Alternatively or additionally, the sensor(s) 822 can be disposed on an internal surface of the coupler 820 opposite the platform 829. The sensor(s) 822 can be structurally and/or functionally similar to the sensor(s) 122. For example, the sensor(s) 822 can be configured to measure one or more signals, e.g., forces and/or loads, etc.

The device 800 can also include one or more sensor(s) that are disposed at other locations on the toilet. For example, while not depicted in the partial view of the toilet in FIG. 6, the device 800 can include sensors disposed at one or more support(s), similar to the sensor(s) 132 described with reference to FIG. 1A. The sensor(s) 822, collectively with other sensors disposed along the toilet, can be configured to measure one or more signals (e.g., forces and/or loads, etc.) such that information (e.g., weight, BCG data, etc.) about an individual or subject seated on the toilet can be accurately determined (e.g., by an onboard or remote processor, as described above).

Figure 7A:
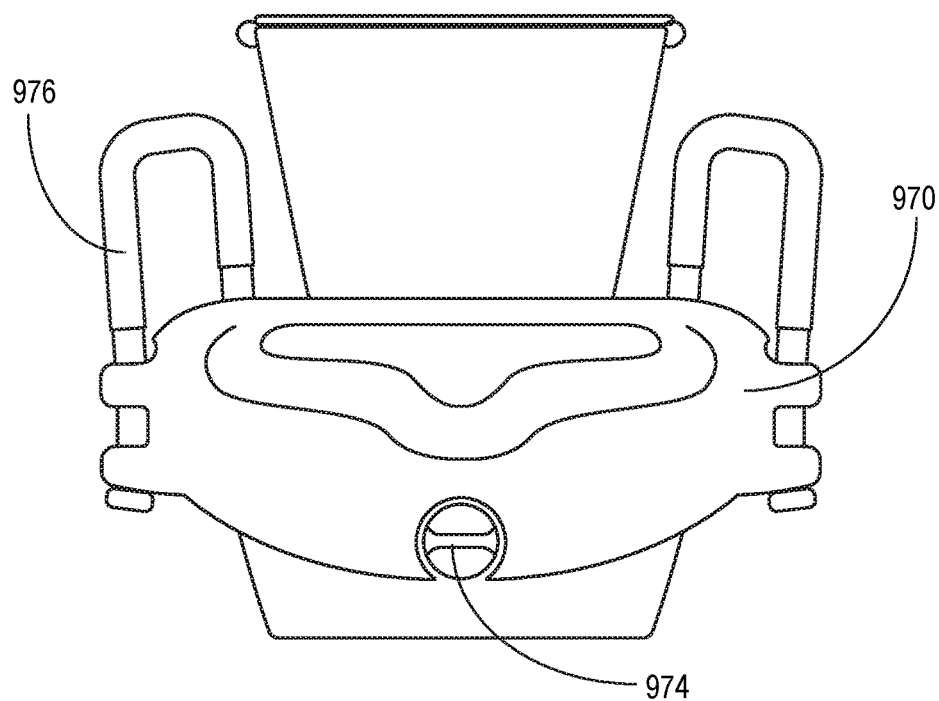
FIGS. 7A and 7B depict a front view and perspective view, respectively, of a device for monitoring one or more loads or forces on a toilet according to an embodiment.
Figure 7B:
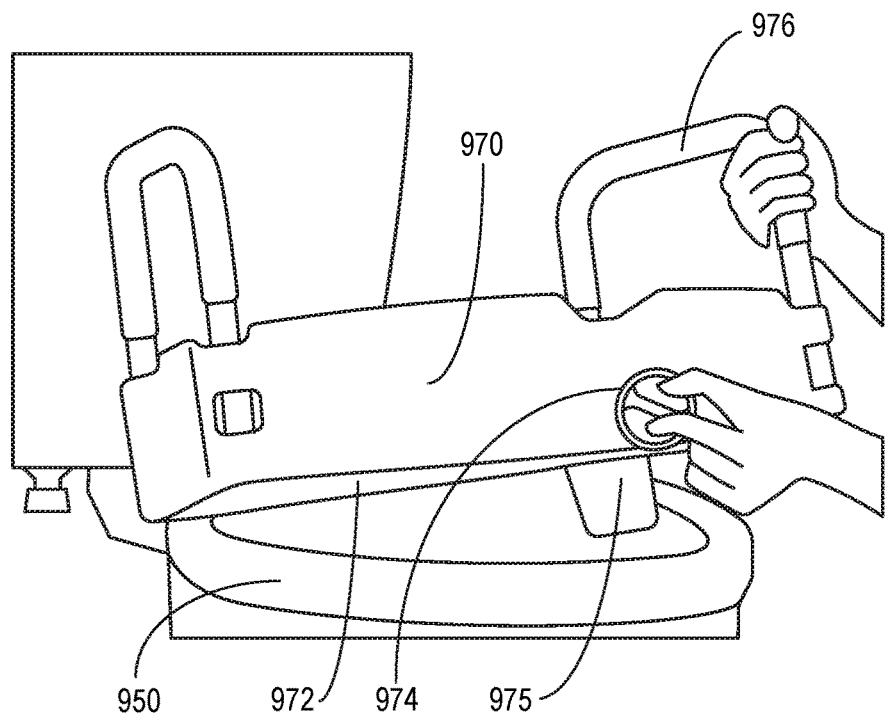

FIGS. 7A and 7B show a schematic illustration of a sensing device implemented as a seat attachment 970, which can monitor signals, such as loads and/or forces, on a toilet, according to some embodiments. The seat attachment 970 can be structurally and/or functionally similar to the seat attachment 170 described above with reference to FIG. 1B. While not specifically identified in FIGS. 7A and 7B, the sensing device can also include one or more sensors located on other portions of the toilet, such as ones located on a ring or a coupler of the toilet and described with reference to FIGS. 1A, 5, and 6.

The seat attachment 970 can be connected to a base 950 of the toilet, e.g., by a coupling mechanism. In some embodiments, the coupling mechanism can include an adjustable knob 974 and a rear wing 975, as shown in FIG. 7B. Tightening the adjustable knob 974 by hand can cause the rear wing 975 to clamp to the upper portion of the base 950, securing the seat attachment 970 against the base 950 and restricting its movement with respect to the base 950. Alternatively, in some embodiments, the seat attachment 970 can be connected to a ring of the toilet instead of the base 950, e.g., by a suitable coupling mechanism. The seat attachment 970 can be removable from the toilet, e.g., to facilitate cleaning of the toilet and/or to move the seat attachment 970 to another toilet. In some embodiments, the seat attachment 970 can include two handles 976 to provide a secure grip for added stability when an individual or subject is lowering or raising from the seat attachment 970. In some embodiments, the handles 976 can be removable, e.g., for storage and/or cleaning.

The seat attachment 970 can include one or more sensor(s) 972 disposed within the seat attachment 970 and/or disposed on a surface of the seat attachment 970. The sensor(s) 972 can be structurally and/or functionally similar to the sensor(s) 172 described with reference to FIG. 1B. For example, the sensor(s) 972 can be configured to measure one or more parameters, e.g., forces and/or loads, BCG data, etc. In some embodiments, the sensor(s) 972 can include a plurality of sensors 972 distributed about the seat attachment 970 such that the sensors can measure forces and/or loads around the seat attachment 970 when an individual or subject is seated on the seat attachment 970.

Figure 8:
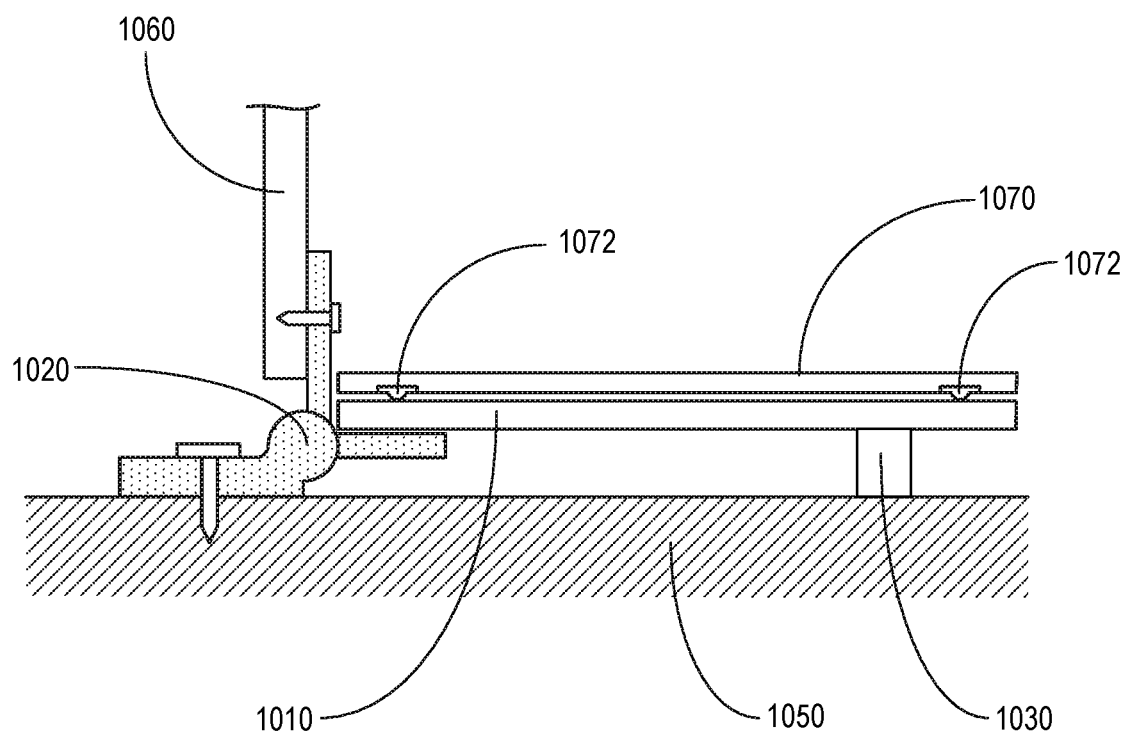
FIG. 8 depicts a side view of a device for monitoring one or more loads and forces on a toilet according to an embodiment.

FIG. 8 shows a schematic illustration of a sensing device implemented as a seat attachment 1070, which can monitor signals, such as loads and/or forces on a toilet, according to some embodiments. The seat attachment 1070 can be structurally and/or functionally similar to the seat attachment 170 described above with reference to FIG. 1B. While not specifically identified in FIG. 8, the sensing device can also include one or more sensors located on other portions of the toilet, such as ones located on a ring or a coupler of the toilet and described with reference to FIGS. 1A, 5, and 6.

The toilet, similar to other toilets described herein, can include a ring 1010, a coupler 1020, one or more support(s) 1030, a base 1050, and a lid 1060. The seat attachment 1070 can be coupled to be coupled to the ring 1010 by one or more flexible couplers (not shown) made of suitable materials such as plastic, rubber, elastomers, and the like. The couplers can secure the seat attachment 1070 to the ring 1010 and prevent lateral movement of the seat attachment 1070 relative to the ring 1010 while allowing for a degree of vertical movement, e.g., as required to impart a force on one or more sensors. In some embodiments, the seat attachment 1070 can be made of the same materials or substantially the same material as the ring 1010, while in other embodiments, the seat attachment 1070 can be made of a material different from that used to fabricate the ring 1010.

In some embodiments, the seat attachment 1070 can be removably attached to the ring 1010 to facilitate cleaning and/or installing the seat attachment 1070 to the toilet. In some embodiments, the seat attachment 1070 can be designed as a portable component, such as a component that is lightweight and/or compact (e.g., thin, foldable). The portable seat attachment 1070 can then be moved to different toilets, enabling a user to monitor information using the sensing device at multiple toilets.

The seat attachment 1070 can include one or more sensor(s) 1072 disposed within the seat attachment 1070 and/or disposed on a surface of the seat attachment 1070. The sensor(s) 1072 can be structurally and/or functionally similar to the sensor(s) 172. For example, the sensor(s) 1072 can be configured to measure one or more parameters, e.g., forces and/or loads, BCG data, etc. In some embodiments, the sensor(s) 1072 can include a plurality of sensors 1072 distributed about the seat attachment 1070, such that the sensors 1072 can measure forces and/or loads around the seat attachment 1070 when an individual or subject is seated on the seat attachment 1070.

While various embodiments described herein are described with reference to a toilet, it can be appreciated that systems, devices, and methods can be used with or integrated into other types of devices, including, for example, a commode.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto; inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

The invention claimed is:

1. An apparatus, comprising:
   a ring configured to be disposed on a base of a toilet, the ring defining an opening for receiving waste therethrough;
   a coupler configured to couple the ring to the base such that the ring can pivot relative to the base, the ring configured to be removably coupled to the coupler;
   a platform integrated into the ring, the platform having a first surface that faces the coupler and a second surface that faces the ring, the first surface configured to be attached to the coupler such that a portion of forces exerted by a subject seated on a surface of the ring when the ring is coupled to the base are transferred via the platform to the coupler; and
   a first sensor disposed on the second surface of the platform, the first sensor configured to measure the portion of the forces exerted by the subject seated on the surface of the ring that are transferred from the ring to the coupler through the platform;
   a set of supports attached to the ring; and
   a set of second sensors disposed within the set of supports, the set of second sensors configured to measure a portion of the forces exerted by the subject seated on the surface of the ring that are transferred from the ring to the base through the set of supports, such that the first sensor and the set of second sensors collectively measure the forces exerted by the subject seated on the surface of the ring.

2. The apparatus of claim 1, further comprising a processor operatively coupled to the first sensor and the set of second sensors, the processor configured to:
   receive first sensor data from the first sensor indicative of the portion of the forces transferred from the ring to the coupler through the platform;
   receive second sensor data from the set of second sensors indicative of the portion of the forces transferred from the ring to the base through the set of supports, and
   determine a ballistocardiogram (BCG) of the subject based on the first and second sensor data.

3. The apparatus of claim 2, wherein the processor is further configured to determine at least one of: a pulse transient time, a blood pressure, a stroke volume, a heart rate, a respiration, a pre-ejection period, or a pulse wave velocity based on the first and second sensor data.

4. The apparatus of claim 1, wherein the coupler is configured to couple near to a first side of the ring and the set of supports are attached near to a second side of the ring opposite to the first side, such that the first sensor and the set of second sensors are distributed about the ring.

5. The apparatus of claim 1, further comprising a lid configured to cover the opening of the ring,
   the coupler configured to couple the lid to the ring and the base such that the lid can pivot relative to each of the ring and the base.

6. The apparatus of claim 1, further comprising the base.

7. The apparatus of claim 1, further comprising at least one of a photoplethysmography (PPG) sensor or an electrocardiogram (ECG) sensor.

8. The apparatus of claim 7, further comprising a processor operatively coupled to the at least one of the PPG sensor or the ECG sensor and being configured to determine at least one of a heart rate, a heart rate variability, a left ventricular ejection time, a pre-ejection period, a flow velocity, a blood pressure, a stroke volume, a cardiac output, a cardiac contractility, an abnormal heart function, a stress level, a respiration rate, or a cardiac waveform characteristic based on data received from the PPG sensor or the ECG sensor.

9. The apparatus of claim 1, wherein the platform is removable from the ring.

10. The apparatus of claim 2, wherein the first sensor is disposed on the second surface of the platform at a rear portion of the ring, and the set of second sensors are disposed on a front portion of the ring,
    the processor further configured to determine a posture of the subject based on a ratio of the first sensor data to the second sensor data.

11. The apparatus of claim 10, wherein the processor is further configured to determine the posture of the subject based on a set of parameters including at least one of a height of the subject, a weight of the subject, an age of the subject, or a gender of the subject.

12. The apparatus of claim 1, wherein the first sensor and the set of second sensors is a group of sensors,
    each sensor from the group of sensors configured to generate an independent signal representative of a portion of the forces transferred from the ring to the base or to the coupler through that sensor when the subject is seated on the surface of the ring, the apparatus further comprising a processor operatively coupled to the group set of sensors, the processor being configured to:

receive the independent signals from the group of sensors;

reduce noise in one or more of the independent signals by comparing the independent signals to one another; and determine a ballistocardiogram (BCG) of the subject based on the independent signals after reducing the noise.

13. The apparatus of claim 12, wherein the processor is further configured to determine a posture of the subject based on the independent signals after reducing the noise.

14. The apparatus of claim 13, wherein the processor is further configured to determine an aortic valve opening based on the ballistocardiogram (BCG) and the posture of the subject.

15. An apparatus, comprising:
a coupler;
a ring configured to be removably coupled to a base of a toilet via the coupler, the ring configured to be disposed on the base of the toilet when coupled to the base of the toilet, the ring defining an opening for receiving waste therethrough, the ring, including:
a body;
a set of supports disposed on a front portion of the body;
a platform disposed on a rear portion of the body, the platform configured to be attached to the coupler via an attachment mechanism such that a portion of forces exerted by a subject seated on the ring when the ring is coupled to the base are transferred via the platform to the coupler;
a first sensor disposed on an internal surface of the body opposite the platform, the first sensor configured to measure the portion of the forces exerted by the subject seated on the ring that are transferred from the ring to the coupler through the platform; and
a set of second sensors included in the set of supports, the set of second sensors configured to measure a portion of the forces exerted by the subject seated on the ring that are transferred from the ring to the base through the set of supports, such that the first sensor and the set of second sensors collectively measure the forces exerted by the subject seated on the ring.

16. The apparatus of claim 15, further comprising a processor operatively coupled to the first sensor and the set of second sensors, the processor configured to:

receive first sensor data from the first sensor indicative of the portion of the forces transferred from the ring to the coupler through the platform;

receive second sensor data from the set of second sensors indicative of the portion of the forces transferred from the ring to the base through the set of supports, and determine a ballistocardiogram (BCG) of the subject based on the first and second sensor data.

17. The apparatus of claim 16, wherein the processor is further configured to determine at least one of: a pulse transient time, a blood pressure, a stroke volume, a heart rate, a respiration, a pre-ejection period, or a pulse wave velocity based on the first and second sensor data.

* * * * *

UNITED STATES PATENT AND TRADEMARK OFFICE
CERTIFICATE OF CORRECTION

| | | |
|---|---|---|
| PATENT NO. | : 12,089,955 B2 | Page 1 of 2 |
| APPLICATION NO. | : 17/885299 | |
| DATED | : September 17, 2024 | |
| INVENTOR(S) | : Nicholas Joseph Conn | |

It is certified that error appears in the above-identified patent and that said Letters Patent is hereby corrected as shown below:

In the Specification

At Column 4, Line number 32:
"embodiments, the shape of the ring 10"
Should read:
-- embodiments, the shape of the ring 110 --

At Column 4, Line number 43:
"base ISO."
Should read:
-- base 150. --

At Column 7, Line number 64:
"the lid 160)"
Should read:
-- the lid 160 --

At Column 10, Line number 28:
"user device(s) 284),"
Should read:
-- user device(s) 280, --

At Column 11, Line number 4:
"network (e.g., Wi-Fi."
Should read:
-- network (e.g., Wi-Fi, --

At Column 11, Line number 41:
"and an input/out device (WO) 246"

Signed and Sealed this
Twenty-fifth Day of February, 2025

Coke Morgan Stewart
*Acting Director of the United States Patent and Trademark Office*

CERTIFICATE OF CORRECTION (continued)
U.S. Pat. No. 12,089,955 B2

Should read:
-- and an input/out device (I/O) 246 --

At Column 13, Line number 20:
"Ater the seat"
Should read:
-- After the seat --

At Column 14, Line number 61:
"toilet including a sensing device 80X)"
Should read:
-- toilet including a sensing device 800 --

At Column 15, Line number 6:
"and base 854)"
Should read:
-- and base 850 --